US006582699B2

(12) United States Patent
Cherwonogrodzky

(10) Patent No.: US 6,582,699 B2
(45) Date of Patent: Jun. 24, 2003

(54) COMBINATION VACCINE FOR ENHANCING IMMUNITY AGAINST BRUCELLOSIS

(75) Inventor: John W. Cherwonogrodzky, Medicine Hat (CA)

(73) Assignee: Her Majesty the Queen in right of Canada as represented by the Minister of National Defence, Ontario (CA)

(*) Notice: Subject to any disclaimer, the term of this patent is extended or adjusted under 35 U.S.C. 154(b) by 179 days.

(21) Appl. No.: 09/735,534

(22) Filed: Dec. 14, 2000

(65) Prior Publication Data

US 2002/0122808 A1 Sep. 5, 2002

Related U.S. Application Data

(60) Provisional application No. 60/170,765, filed on Dec. 15, 1999.

(51) Int. Cl.[7] ...................... A61K 39/00; A61K 39/385; A61K 39/116; A61K 39/02; A61K 39/10

(52) U.S. Cl. ................................ 424/184.1; 424/193.1; 424/197.11; 424/203.1; 424/234.1; 424/252.1

(58) Field of Search .................... 435/252.1; 424/234.1, 424/252.1, 184.1, 193.1, 197.1, 203.1

(56) References Cited

U.S. PATENT DOCUMENTS 5,182,109 A * 1/1993 Tamura et al.
6,444,210 B1 * 9/2002 Kournikakis et al.

OTHER PUBLICATIONS

Lord et al., "Venezuelan Field Trials of Vaccines Against Brucellosis", May 1998, pp. 546–551.

Cherwonogrodzky et al., "A Polysaccharide Vaccine To Enhance Immunity Against Brucellosis", 1995, pp. 29–37.

Weynants et al. (Clin. diagn Lab Immunol 1996 vol.3(3) pp. 309–14).*

Weynants et al. (Infect Immun 1997 vol. 65(5) pp. 1939–1943).*

* cited by examiner

*Primary Examiner*—Mark Navarro
(74) *Attorney, Agent, or Firm*—Nixon & Vanderhye PC

(57) ABSTRACT

A vaccine comprising a combination of Brucella "A" and "M" outer-polysaccharides (OPSs) and "R" protein antigens for enhancing immunity against brucellosis is disclosed. The OPS may be obtained from different strains or species of Brucellae (i.e. combining OPS extracted from different bacteria expressing "A" or "M" OPS, or combining OPS and OPS-protein complexes extracted from different bacteria). The OPS or OPS-protein complexes may also be obtained from a single strain expressing more than one OPS (e.g. from *B. suis* strain 145 which expresses "A", "M" and possibly other OPSs). The vaccine according to the present invention overcomes the limitation of previously discovered *B. abortus* "A" OPS which only protects against species and strains of Brucella that had "A" OPS but not against others with different OPS.

13 Claims, No Drawings

COMBINATION VACCINE FOR ENHANCING IMMUNITY AGAINST BRUCELLOSIS

The present application claims benefit of U.S. Provisional Application Ser. No. 60/170,765, filed Dec. 15, 1999.

FIELD OF INVENTION

The present invention relates to a vaccine, comprising a combination of bacterial components derived either from different species of Brucellae, or one strain expressing different components, that enhances immunity against brucellosis. The vaccine formulations are applicable for one or more cross-reactive bacteria thereof.

BACKGROUND OF THE INVENTION

Brucellosis is a debilitating disease that can cause abortions and weight loss in animals as well as undulating fevers, night sweats, incapacitation and arthritis in humans. It is very hardy to environmental factors, easily aerosolized and infectious through skin abrasions, ingestion and the pulmonary route. It is difficult to treat with antibiotics and often persists as a life-long infection. Brucellosis is a disease endemic to most countries, especially under-developed nations where Brucella species infect 0.1 to 10% of the livestock such as cattle, swine, sheep, goats, and camels. A zoonotic disease, these also infect other domestic animals such as dogs and poultry, wildlife such as bison, caribou and wolves and marine mammals such as whales and dolphins. People are especially vulnerable to infection either through handling infected products or ingesting contaminated foods.

Up-to-date, effective treatment against brucellosis for animals, including humans, has been limited. For humans, administering high doses of combination antibiotics, for example doxycycline with rifampin over long periods, has been found to be effective to clear the disease, but non-compliance and relapses are common. For animals, the cost and limited effectiveness of antibiotic treatments often lead to the decision of either no treatment or elimination of the infected animal and its associated herd.

The most preferred type of disease management is to avoid infection and to reduce the incidence and spread of the disease by vaccination. For livestock, namely cattle, at present vaccination consists of using an attenuated (weakened) vaccine strain such as *Brucella abortus* strain 19. Although it is one of the best vaccines for cattle, it does have limitations in that the vaccine does not give absolute protection and there is about a 20% failure rate, results from serological tests can be confusing for a positive serology may be caused by vaccination, infection, or vaccination with subsequent infection, the vaccine although tolerated by cattle is pathogenic for humans, and on occasion the vaccine does revert to a "wild" or virulent form.

For humans, there existed a French vaccine that consisted of a phenol insoluble residue. However, this vaccine has been discontinued as it was found that the residue caused a high rate of reactogenicity (in one study, a large percentage of the vaccine recipients developed swollen lymph glands and granuloma at the site of injection) and hyper-sensitivity (vaccinates that touched killed Brucella preparations presented symptoms of anaphylactic shock).

Recently, the Applicant has discovered a new vaccine that protected animals (e.g. mice, guinea pigs and swine) from brucellosis and which may upon further development be suitable for protecting humans. The vaccine is as described in U.S. Pat. No. 5,951,987 which is herein incorporated by reference. The vaccine consists of an outer-polysaccharide (OPS) isolated from Brucella such as Brucella abortus. The vaccine protected animals from different strains and species of Brucella tested (e.g. *B. abortus* 30, *B. abortus* 2308 and *B. suis* biovar 1) as well as infections from *Francisella tularensis* live vaccine strain (LVS) which causes tularemia in mice. This gave evidence that the vaccine would likely offer effective protection against infections from a broad spectrum of Brucella species and cross-reactive bacteria. However, it has subsequently been found otherwise. Although the *B. abortus* OPS vaccine was effective in offering animals protection from brucellosis, it did so only against species and strains that resembled *B. abortus* in serology (i.e. had "A" OPS antigens). It did not appear to be effective against species and strains that resembled *B. melitensis* in serology (i.e. had the "M" or "A&M" OPS antigens). Hence, there still remains a need for a vaccine which is effective against infections from a wide spectrum of Brucella species.

SUMMARY OF THE INVENTION

In accordance with one aspect of the present invention, there is provided a vaccine comprising a combination of Brucella "A" and "M" outer-polysaccharides and "R" protein antigens. The outer-polysaccharides may be obtained from the same or different species of Brucellae. The most preferred source of OPS is derived from Brucella but a logical extension of this finding is to use bacterial species cross-reactive thereof.

The combination may be obtained from combining "A" outer-polysaccharides extracted from Brucella species selected from the group consisting of *B. abortus* biovar 1, *B. abortus* biovar 2, *B. abortus* biovar 3, *B. abortus* biovar 6, *B. melitensis* biovar 2, *B. suis* biovar 1, *B. suis* biovar 2, *B. suis* biovar 3, *B. neotomae* and *B. maris;* "M" outer-polysaccharide extracted from Brucella species selected from the group consisting of *B. abortus* biovar 4, *B. abortus* biovar 5, *B. abortus* biovar 9, *B. melitensis* biovar 1, *B. suis* biovar 5; and "R" core polysaccharide and proteins extracted from Brucella species selected from the group consisting of *B. ovis* and *B. canis.*

Alternatively, the combination may be obtained by combining "AM" outer-polysaccharides extracted from Brucella species selected from the group consisting of *B. abortus* biovar 7, *B. melitensis* biovar 3 and *B. suis* biovar 4 (note: *B. suis* 145 biovar 4 is used in the present patent submission), and "R" core polysaccharide and protein extracted from Brucella species selected from the group consisting of *B. ovis* and *B. canis.*

In accordance with another aspect of the present invention, there is provided a vaccine comprising a combination of Brucella outer-polysaccharides containing the "A" and "M" antigens and a Brucella outer-polysaccharide-protein complex.

In this case, the combination may be obtained by combining "A" outer-polysaccharide purified from Brucella species selected from the group consisting of *B. abortus* biovar 1, *B. abortus* biovar 2, *B. abortus* biovar 3, *B. abortus* biovar 6, *B. melitensis* biovar 2, *B. suis* biovar 1, *B. suis* biovar 2, *B. suis* biovar 3, *B. neotomae* and *B. maris;* "M" outer-polysaccharide purified from Brucella species selected from the group consisting of *B. abortus* biovar 4, *B. abortus* biovar 5, *B. abortus* biovar 9, *B. melitensis* biovar 1, *B. suis* biovar 5; and an outer-polysaccharide-protein complex selected from the group consisting of outer-polysaccharide and Brucella membrane proteins, outer-polysaccharide and Brucella surface proteins, outer-polysaccharide and Brucella surface enzymes and outer-polysaccharide and Brucella cytoplasmic proteins.

Alternatively, the vaccine may be obtained by combining "AM" outer-polysaccharides extracted from Brucella species selected from the group consisting of *B. abortus* biovar 7, *B. melitensis* biovar 3 and *B. suis* biovar 4, and an outer-polysaccharide having a protein selected from the group consisting of Brucella membrane proteins, Brucella surface proteins, Brucella surface enzymes and Brucella cytoplasmic proteins.

The vaccine may consist of 1 ng to 10 ug, preferably 1 ug, of each of the OPS forming the combination for vaccination of mice weighing about 20 grams.

The vaccine is effective as a prophylactic treatment from infection against a wide range of Brucella species namely *B. abortus, B. melitensis* and *B. suis.* By logical extension the vaccine is likely to be effective for the prevention of brucellosis from *B. ovis, B. canis, B. neotomae* and *B. maris.* Animal studies support its use as a vaccine for livestock, and with further development possibly as a vaccine for humans. It is most effective by intra-peritoneal, sub-cutaneous and intramuscular administration. It is least effective when given intra-nasally. The vaccine works best against the most virulent species and strains of Brucella, most of the healthy vaccinates having no bacteria in their spleens or having a million fold less bacteria than controls. The vaccine works, but is less effective where it is not needed, or in mice given Brucella species and strains of low virulence.

Serum or white blood cells of mammals vaccinated with the vaccine in accordance with the present invention prevented brucellosis in recipient animals. Protection is long term (i.e. at least several weeks) but unlike other vaccines it is also protective in the short term (i.e. protective in 1 day or less).

DETAILED DESCRIPTION OF THE INVENTION

Brucella species can be classified by their different type of outer-polysaccharides (OPS). These serological types are those having the "A" OPS, the "M" OPS and those lacking OPS or the "R" group (i.e. antigens are predominantly protein with some antigenicity being the "core" polysaccharides attached to the lipopolysaccharide, or LPS, lacking OPS), wherein "A", "M" and "R" stands for the type of antigens. Some species also express more than one antigen, for example some strains of *B. suis* (biovar 4) which express both the "A" and "M" antigens, and some are capable of changing their antigens within the same host (personal communications, Dr. G. G. Schurig, 1997). The various types of OPS are very similar in chemical structures. They are generally made of identical sugars, which are linked differently. Because of the similarity between the OPS and the considerable cross-reaction between the "A" and "M" OPS of Brucella, one would expect a single OPS vaccine, i.e. a vaccine consisting of one type of OPS, to be effective against a wide range of Brucella species. This, however, was found to be only partially true. The Applicant discovered that a combination or "cocktail" vaccine, i.e. a vaccine having a combination of the different OPS, is much more effective than the single OPS vaccine in providing protection against a wide spectrum of Brucella species.

To be most effective, the cocktail or combination vaccine should include a range of OPS, for example both "A" and "M" OPS, and "R" antigens. As it is likely that one or more OPS, other than "A" and "M", are also produced (Vizcaino, N., Cloeckaert, A., Zygmunt, M. S., and Fermandez-Lago, L. 1999. Molecular characterization of a Brucella species large DNA fragment deleted in Brucella abortus strains: evidence for a locus involved in the synthesis of a polysaccharide. *Infection and Immunity,* 67: 2700–2712), the inclusion of these would likely offer greater protection.

The cocktail or combination vaccine may be replaced by an outer-polysaccharide-protein complex. Brucellae can attach proteins (the "R" antigen, which can also be extracted from cells that do not express the "A" or "M" antigen, have colonies rough in appearance and express mainly proteins) to OPS. OPS and OPS-protein complex can be separated (e.g. with 0.2 M trichloroacetic acid, OPS remains soluble, OPS-protein precipitates).

Outer-polysaccharides containing the "A" antigen can be obtained from *B. abortus* biovar 1, *B. abortus* biovar 2, *B. abortus* biovar 3, *B. abortus* biovar 6, *B. melitensis* biovar 2, *B. suis* biovar 1, *B. suis* biovar 2, *B. suis* biovar 3, *B. neotomae* and *B. maris.*

Outer polysaccharides containing the "M" antigen can be extracted from *B. abortus* biovar 4, *B. abortus* biovar 5, *B. abortus* biovar 9, *B. melitensis* biovar 1, *B. suis* biovar 5.

Proteins, core polysaccharides and short chained outer-polysaccharides comprising the "R" antigen can be purified from *B. ovis* and *B. canis.*

Outer-polysaccharides containing both the "A" and "M" antigens can be purified from *B. abortus* biovar 7, *B. melitensis* biovar 3 and *B. suis* biovar 4.

Suitable proteins for the "R" component are Brucella proteins. Preferably, they are outer-membrane proteins (opm) such as opm1, opm2 and opm3, lipoprotein linked to cell wall, porin (a protein that allows ions or metabolites through the membrane), A5 on the cell surface, surface proteins such as a, b and X, surface enzymes such as protease, Brucellin proteins and internal or cytoplasmic proteins. Other proteins may be mannosyltransferase, GDP-mannose 4,6 dehydratase, perosamine synthetase, ABC-type transporter and formyl transferase. Additional proteins such as those identified in the paper "Conservation in Brucella spp. of seven genes involved in the biosynthesis of the lipopolysaccharide O-chain", A. Cloeckaert, M. Grayon, J-M Verger, J-J Letesson and F. Godfroidt, 1998. 51th Annual Brucellosis Meeting, Chicago, herein incorporated by reference, can also be used.

To assess the effectiveness of the vaccine, different single OPS vaccine and combination OPS vaccines were prepared and tested. The novel formulation of using combination OPS vaccine of the present invention is shown to be more effective than a single OPS vaccine formerly disclosed by the Applicant in the U.S. Pat. No. 5,951,987.

Materials and Methods

Bacterial Cultures

*B. abortus* 30, *B. abortus* 2308, *B. melitensis* 16M and *B. suis* 145 were acquired in 1989 from the Animal Diseases Research Institute (ADRI-Nepean, now the Canadian Food Inspection Agency), Nepean, Ontario, Canada. The bacteria were thawed and small aliquots of the materials were obtained and grown on Brucella agar (Difco Laboratories, Detroit) with 1.5 ppm crystal violet at 37° C., 5% $CO_2$, 90% humidity, for 1 week. A loopful (about a billion cells) of the culture were placed in vials containing 1 ml of sterile Brucella broth with 15% glycerol and the vials were frozen at −70° C. As required, vials containing *B. melitensis* 16M, *B. suis* 145, *B. abortus* 30 and 2308 were thawed and subcultured onto, for example, Brucella agar and incubated to provide cells for Protect Beads™ storage, or into Brucella broth and incubated to provide cells which were later used in the infectivity experiments.

Representative vials of the bacteria were thawed and used to inoculate Brucella agar slants (2 cc agar in a 5 cc vial). The cultures were verified on May 10, 1999 by the National Veterinary Services Laboratories (Ames, Iowa), which confirmed that the vials containing *B. abortus* 30 or *B. abortus* 2308 belonged to *B. abortus* biovar 1 ("A" antigen predominant), *B. melitensis* 16M belonged to *B. melitensis* biovar 1 ("M" antigen predominant), *B. suis* 145 belonged to the atypical *B. suis* biovar 4 (has both "A" and "M" antigens).

The bacteria used to cause Brucella infection were prepared by inoculating bacteria such as *B. melitensis* 16M into Brucella broth (Difco Laboratories, Detroit), grown overnight, then 0.010 ml was transferred to 100 ml Brucella broth and used within 18 hours of incubation. This method revealed more effective in providing bacteria with high virulence than the conventional method of simply thawing a frozen stock of bacteria and determining the colony forming unit (CFU), or adding the thawed stock to prewarmed Brucella broth and incubating for 2 hours at 37° C., 5% $CO_2$ and 90% humidity.

The best way to ensure virulence of the bacterium (e.g. *B. melitensis* 16M) was to passage it through sets of 5 mice. Hence a culture that appeared to have lost its virulence, would be given to each of 5 mice by intra-peritoneal injection. In this case, each mouse was given $5\times10^4$ to $5\times10^5$ bacteria/0.1 ml sterile saline. After 1 week, the mice were sacrificed, their spleens weighed and crushed in saline, and serially diluted and plated on Brucella agar with 1.5 ppm crystal violet and incubated for 2 hours at 37° C., 5% $CO_2$ and 90% humidity and the colony forming unit was determined. Bacteria on these plates that were from the mouse with the largest spleen size and greatest bacterial number in the spleen was selected and these were used to infect another 5 mice and the selection was repeated. Within 3 passages, the bacterium had exceptional virulence (caused large spleens, 3–5 fold larger than normal, and high bacterial numbers, about 3 million bacteria per spleen). These bacteria were used only for a few experiments as it was viewed that passage through an animal could introduce other unknown variables.

Vaccine Preparation a) Preparation of "A" OPS, "M" OPS or OPS-protein Vaccines

The method of preparation for some of the vaccines (e.g. "A" OPS from *B. abortus* 1119-3, "M" OPS from *B. melitensis* 16M) was as previously described ("Antigens of Brucella", J. W. Cherwonogrodzky et al., pages 54–55, In: K. Nielsen, J. R. Duncan (ed.) 1990 Animal Brucellosis CRC Press, Boca Raton). Briefly, each bacterium was grown on about 90 ml of Brucella agar with 1.5 ppm crystal violet into each of twenty 150 $cm^2$ sterile tissue culture flasks and incubated for 2 hours at 37° C., 5% $CO_2$ and 90% humidity. After the incubation period, 5 ml of sterile 3% acetic acid with 1% saline was added to each flask, a dozen small glass beads were added, and the cells made into a suspension by rocking or lightly shaking the flask as required. The suspension was removed with a pipette and placed into a 250 ml centrifuge bottle. Another 5 ml of sterile acetic acid with saline in triply distilled water was added to the flask. The flask was rocked or shaken as required, and the suspension was added to the previous one.

Once all twenty flasks were processed, the suspension was shaken vigorously, and stored at 4° C. for at least one week. Thereafter, it was autoclaved at 121° C., 15 psi for 2 hours with a loosened cap. Once autoclaved and cooled, the bottle was centrifuged at 15,000×g for 30 min at 4° C. The supernatant was kept and the cells discarded.

The supernatant was neutralized with 10 M NaOH and had 2 M trichloroacetic acid (TCA) added to a final concentration of 0.2 M TCA. This was centrifuged (20,000×g, 30 min, 4° C.). The OPS remained soluble in the supernatant, the OPS-protein that was precipitated by the TCA was in the pellet. The pellet was resuspended in triply distilled water. Both the supernatant and the redissolved pellet (kept separate) were extracted with equal volumes of liquified phenol (90% phenol with 10%water) added. The mixture was magnetically stirred for 30 min at 70° C. and was chilled at 4° C. overnight. The bottom phenol layers were removed and centrifuged as before to remove debris or the remaining water layer. To the phenol layers were added 5 volumes of methanol with 1% sodium acetate to enhance precipitation and this was chilled overnight at 4° C. The preparations were centrifuged as before, washed twice more with a similar volume of methanol-acetate, and the pellet was dissolved in triply distilled water and dialyzed (1000 mw cutoff) against triply distilled water. Once dialyzed, these samples were centrifuged to remove denatured material and lipopolysaccharide (LPS, this aggregates in distilled water while outer-polysaccharide (OPS) remains soluble). The samples were freeze-dried, weighed and kept at −70° C. until required. The resulting samples were at least 90% pure.

b) Preparation of *B. suis* 145 OPS Vaccine

When the previous method for OPS preparation was applied to *B. suis* 145, it was unsuccessful. Neither OPS nor OPS-protein precipitated when methanol-acetate was added to the phenol extracts. The material was still present, as evidenced by OPS and OPS-protein precipitating when the phenol/methanol-acetate solutions were kept at −20° C. instead of 4° C. for a week, but it was clear that the procedure had to be changed to prepare OPS or OPS-protein for vaccines. (It was subsequently found that *B. suis* 145 OPS is more heterogeneous in composition than the other Brucella OPS cited, explaining the failure of the previous method, Dr. Brad Berger, unpublished results.)

In brief, *B. suis* 145 was grown on agar medium (Brucella agar, with or without 1.5 ppm crystal violet, trypticase soy agar, with or without 1.5 ppm crystal violet, gave similar results) in sterile 150 cm tissue culture flasks, at 35° C., 5% $CO_2$ and 90% humidity for 1 week. After this time, cells were both killed and removed by adding 5 ml of 5% phenol/1% saline, adding glass beads, and rolling or shaking the flask to dislodge the cells, removing the cells, adding another 5 ml of phenol-saline, rolling and shaking the flask again, and pooling cell suspensions. From 400 flasks, about 250 grams wet weight of cells was removed and the final volume was about 3 liters in sixteen 250 ml centrifuge bottles. The suspension was kept 1 week at 4° C., with occasional shaking, to ensure release of loosely bound antigens.

After 1 week, the suspension was centrifuged (15,000×g, 20 min, 4° C.), the supernatants pooled, and the cells washed with a small volume (40 ml per centrifuge bottle, centrifugation as before) of phenol-saline. The liquid was added to the pooled supernatants.

To the supernatant, glacial acetic acid was added to a final volume of 3%. This suspension was then placed in a boiling water bath for 2 hours. It was left to cool to room temperature for a day. The pH was not adjusted (the low pH appears to enhance precipitation at a later methanol stage). A one-half volume of 90% phenol (10% water) was added (the smaller volume concentrates the OPS). This was magnetically stirred on a magnetic hot-plate until the temperature rose to the mixture's "clarity" point (the phenol-water mixture was opaque, but around 65–70° C. the phenol and water dissolved into each other, causing the mixture to clear). It was then allowed to cool at 4° C. overnight, centrifuged and the phenol layer (bottom layer, usually dark red in colour) kept. A 2-week sterility check is done to ensure this phenol layer is sterile and it is then taken out of Biocontainment 3. Once in the general laboratory area, the phenol was chilled overnight at 4° C. as was the methanol-acetate (methanol with 1% sodium acetate.$3H_2O$). Five volumes of methanol-acetate was added to the phenol layer, this was mixed on a magnetic stirrer and allowed to settle for 1–2 days. After this time, most of the liquid above the precipitate was aspirated away (the flask is placed on ice to prevent mixing if it begins warming to room temperature). The remaining preparation was centrifuged as before, the supernatant discarded, and the pellet resuspended in methanol-acetate (a saw-toothed OmniMix™ is best for blending the suspension) and centrifuged. The pellet was then resuspended in distilled water, placed in a 1000 mw cutoff dialysis cellulose membrane, and dialyzed against distilled water at 4° C. (From the frothing that occurred when the outside water was discarded during changes, it appeared that considerable amount of small m.w. OPS was lost in this process, but that a large amount of larger m.w. OPS was retained by the dialysis.) After dialysis, the preparation was removed from the dialysis bag, and centrifuged to remove denatured material. The pellet of denatured material was discarded, the supernatant was kept, and to the latter 2 M trichloroacetic acid (TCA) was added until the final concentration was 0.2 M TCA. This was then centrifuged. Both the supernatant (containing OPS) and the pellet (containing OPS-protein, this was suspended in distilled water) were dialyzed against distilled water. After extensive dialysis, each preparation was centrifuged to remove denatured or particulate material. The solutions were then aliquoted and freeze-dried. The OPS could be further refined with enzyme digestion (though the starting material was at least 90% pure, having no detectable A260/A280 nm absorbing nucleic acids and only about 0.6% protein) and ultra-centrifugation (120,000×g, 4° C., 3 hours) to remove trace amounts of LPS.

For the washed *B. suis* 145 cells noted previously, these were suspended in 3% acetic acid and 1% saline (for every gram of cells, 5 ml of acetic acid-saline was added) and placed in a boiling water bath for 2 hours with swirling to mix the suspension every half hour. The cells were left for a day to cool to room temperature. The preparation was centrifuged, and the supernatant kept. The cells were mixed in an equal amount (w/v) of acetic acid saline, centrifuged, and the liquid pooled with the other. A phenol extraction was done (half a volume of phenol was used with the cell supernatant) on this liquid as noted before. The OPS released from the cell by boiling water was by the method noted above.

The cells from the above were resuspended in 5 volumes of acetic acid-saline, autoclaved (121° C., 15 psi, 2 hours), cooled, centrifuged, and the liquid (as well as a washing of the cells with an equal amount of acetic acid-saline which was added) was processed as before. The different fractions noted above have been tested (1 ug/0.1 ml sterile saline/mouse, intraperitoneal injection). All OPS fractions and all OPS-protein fractions were protective (about 10,000 fold less bacteria in their spleens than controls 1 week after challenge). The whole cell with OPS removed, or the interphase material (between the phenol and water layers during extraction) were not protective (indeed, the interphase material was immuno-suppressive, causing mice to have about 5-fold more bacteria in their spleens than non-vaccinated control mice).

About 4-fold more OPS was acquired if the *B. suis* 145, was passaged through a mouse before being grown on agar. There was also a considerable amount of brown gelatinous material on the cells after autoclaving (about 20 c.c. on 250 grams of cells, when 2 cc of this was freeze-dried and gave 80 mg dry weight). However, as passaging through a mouse might be introducing new variables, frozen stocks kept on ProtectBeads™ at −70° C. were used as the inoculum for OPS and OPS-protein production.

The strength for using *B. suis* 145 as a source of vaccine is that as it expresses both "A" and "M" OPS (as well as Brucella "R" proteins) it is also likely to express other OPS. Recently another OPS has been isolated, by a method unobvious to anyone skilled in the art. There was an insufficient amount of this polysaccharide to characterize, other than it was polysaccharide, but animal studies showed that this OPS (which is in the OPS vaccine preparation) also protects mice from brucellosis (Dr. Brad Berger, unpublished results).

As stated previously in this text, the *B. suis* 145 OPS or OPS-protein preparations were found to be potent vaccines that protected mice from brucellosis. Against the most virulent strains and species of Brucella, vaccinated mice often had no bacteria in their spleens, or only a few (i.e. a million fold less than controls). For the latter, it was unknown if these were simply the last traces of the challenge that were soon to be cleared (which is likely for their growth lag on agar medium suggests that these are heavily damaged by the immune system of the host) or whether these were mutants with polysaccharides different from what the mice were vaccinated against. These "survivors" were allowed to continue growing on the agar plates previously used to assess spleen bacterial loads (35° C., 5% $CO_2$, 90% humidity, for an additional 3 weeks), these were scraped from the plates and suspended (3.3 grams wet weight of cells was recovered) in 5% phenol, 1% saline (50 ml) and processed as noted above. Mice have been vaccinated with *B. suis* 145 OPS (as noted above, 1 ug/mouse by intraperitoneal injection), or OPS prepared from *B. suis* 145 bacterial "survivors" from vaccinated mice that were challenged (1 ug/mouse by i.p.), or *B suis* 145 OPS+*B. suis* 145 "survivors" OPS (both 1 ug/mouse by i.p.). This study is underway but at the time of this patent submission it has not determined if the OPS from bacterial "survivors" is equivalent to *B. suis* 145 OPS for protecting mice from brucellosis or whether it acts synergistically to enhance vaccine efficacy.

Mice

Unless otherwise specified, mice were 19–21 grams at the start of the experiment. They were female balb/c mice obtained from Charles River, St. Contance, Quebec, Canada.

Vaccination

Mice were vaccinated intra-peritoneally (i.p) into the lower right side of the belly, sub-cutaneously (s.c.) into the nape of skin bunched on the back, intramuscularly (i.m) into the upper left leg or intra-nasally (i.n.). The intra-nasal route required mice to be anaesthetized with Metofane™. Generally, the vaccines comprised OPS from *B. abortus* 1119-3, *B. melitensis* 16M and/or *B. suis* 145 in sterile saline as a single dose per mouse, or a combination of OPS and OPS-protein. For example, a single antigen vaccine can be 1 ug of *B. suis* OPS in 0.1 ml sterine saline as single dose per mouse. An example of a combination vaccine can bel ug each of *B. abortus* OPS+1 ug *B. melitensis* OPS-protein+1 ug *B. suis* OPS together in 0.1 ml sterile saline as a single dose per mouse. Typically, for intra-peritoneal, sub-cutaneous and intra-muscular injections, the OPS were diluted in 0.1 ml sterile saline, whereas for intra-nasal installation these were in 0.01 ml (half given into each nostril). Unless otherwise specified, mice were allowed to rest for 5 weeks before challenge.

Oral administration of the vaccine was proven to be effective in the case of *B. abortus* OPS vaccine to swine in Venezuela (U.S. Pat. No. 5,951,987). While the Applicant did not test oral administration of the new vaccine formulations of the present invention, it is suggested that efficacy of these vaccines do extend to oral administration.

Challenges

For intra-peritoneal challenge, a culture of Brucella was diluted serially in 9 ml sterile saline blanks and $5\times10^5$ bacteria (as confirmed by plating) in 0.1 ml of sterile saline was given to each mouse. The mice were allowed to rest for 1 week before being sacrificed and assessed. Past studies suggested that infection by intra-nasal inoculation was more difficult to take place (Cherwonogrodzky J. W., and Di Ninno, V. L. 1994, Brucella, brucellosis, undulant fever, AB—Is it a threat? A review in question and answer form (U), Suffield Memorandum 1434, Defence Research Establishment Suffield, UNCLASSIFIED, page 6). Therefore, for intra-nasal challenge, 0.010 ml of a culture broth at an early phase of growth (about $5\times10^7$bacteria/0.010 ml) was used without dilution and the mice were allowed to rest for 2 weeks rather than 1 week before being sacrificed and assessed.

Assessment of Infection

Mice seldom show any symptoms when infected with Brucella, although with the more serious strains they may show ruffled, grayish looking fur. Hence the only way to assess infection, was to weigh each mouse, sacrifice these by cervical dislocation and remove organs such as spleens for weighing and obtaining bacterial counts. In this case, the spleens were weighed for the ratio spleen wt/body wt., then crushed in 1 ml sterile saline by hand with a glass tissue grinder (Wheaton, 2 ml volume). This suspension was removed, another 1 ml sterile saline was added to the chamber and crushing continued to complete the task and to rinse the inside of the chamber. This second 1 ml, was pooled with the first. To prevent possible aerosol generation, the work was performed inside a Biosafety 2a or 2b Cabinet inside a Biocontainment Level 3 (BL-3) area, and the investigator wore a seam sealed positive pressure hood (3M), HEPA filter with a blower powered by a battery pack, a sealed Tyvek overall, double gloves and boots. Five tissue grinders were used for each group of mice and these were sterilized between groups. Each tissue grinder had the chamber filled with 70% ethanol and the grinding handle inserted therein. The chamber was topped up with 70% ethanol, sprayed with the ethanol to decontaminate the outside and then allowed to sit for 30 minutes. Thereafter, the ethanol was poured out, the top of the chamber and the grinding handle wiped with a KimWipe™ soaked in 70% ethanol and the grinding handle allowed to air dry. The ethanol was removed from the chamber with a sterile pipette and the chamber rinsed with sterile saline. Any adhering liquid was removed with another sterile pipette. For the crushed spleen in 2 ml of saline noted above, 0.1 ml of this was plated onto a plate of Brucella agar with 1.5 ppm of crystal violet, and 1 ml was transferred to a 9 ml sterile saline blank and dilutions with plating were repeated for these. Plates were incubated for 2 hours at 37° C., 5% $CO_2$ and 90% humidity and the CFU counted after one week incubation.

Separation of Blood Components

In instances where only serum was required, mice were given a double dose of 1:14 diluted Somnitol™ (pentabarbitol), in 0.5 ml per mouse. Once anesthetized, a heart puncture was done with a 1 ml syringe fitted with a 26-gauge needle, and whole blood was removed. Mice did not recover from the amount of anaesthetic given. The blood was transferred to a 1.5 ml Eppendorf™ microcentrifuge tube and the tube was left in the refrigerator at 4° C. for a few hours to clot. It was then vortexed briefly to loosen the clot and centrifuged at 2000×g for 5 minutes at room temperature or at 22° C. to separate the serum, which formed the top layer, from blood cells. The serum was removed with a Pasteur pipette, pooled with serum from other mice in the group, and filtered through a 0.2 um filter. It was used within a few hours of preparation.

To fractionate serum into different molecular weight groups, whole serum (about 10 ml from 20 vaccinated mice) was placed initially into a 1000 molecular weight (m.w.) cutoff dialysis bag, and dialyzed in a 100 ml graduated cylinder against distilled water with magnetic stirring within a 4° C. refrigerator. After 24 hours, the dialysate (1000 or less m.w. components), which remained in the cylinder, was frozen and freeze-dried. The serum was transferred to a 12,000 m.w. cutoff dialysis bag and dialyzed as before. This dialysate was 1,000–12,000 m.w. and freeze-dried. The serum within the dialysis bag had 12,000 or greater m.w. components and was freeze-dried.

To separate blood components, initially 1 ml of sterile saline was added to a 10 ml blood collection tube with heparin (10 fold heparin). One-tenth ml of 10-fold heparin was drawn into the 1 ml syringe used to collect mouse blood. Whole blood (2 ml) was layered onto an equal volume of Lymphoprep™ (Accurate Chemical and Scientific Corporation, Westbury, N.Y., USA) and centrifuged 1000×g for 30 minutes at room temperature. The top layer was serum which was drawn off with a Pasteur pipette and then filtered through a 0.2 $\mu$m filter (final volume was about 1.5 ml). Mononuclear and polymorphonuclear cells formed 2 bands within the dextran solution. These were both drawn by a Pasteur pipette and washed twice with sterile saline (diluted in 0.85% sterile saline) and centrifuged 2000×g for 30 min at room temperature. The supernatant layer was discarded and the cell pellet resuspended in 5 ml sterile saline, and washed as before and the cell pellet was resuspended in 1 ml sterile saline. The red blood cell pellet was removed, washed with sterile saline and resuspended in 1.5 ml of sterile saline.

The averages and standard error about the mean were calculated using the GraphPad Instat program (version 1.14).

RESULTS AND DISCUSSION

EXAMPLE 1

Cross-protection Study

In this study, female balb/c mice were injected intraperitoneally (i.p.) with either 0.1 ml sterile saline or *B. abortus* OPS vaccine/0.1 ml sterile saline. The mice were challenged 5 weeks later with $5\times10^{5(delete4)}$ bacteria/0.1 ml sterile saline. They were sacrificed and assessed one week later. The results are shown in Table 1.

TABLE 1

Cross-protection study using a previous vaccine formulation

| Group of mice (5 mice/group) | Spleen size | Average number of bacteria (CFU)/spleen |
|---|---|---|
| Control: mice infected with *B. abortus* 2308 | Normal | 13,200 ± 4,170 |
| Mice vaccinated with 1 ug OPS, infected with *B. abortus* 2308 | Normal | 5,960 ± 2,440 |
| Mice vaccinated with 100 ug OPS, infected with *B. abortus* 2308 | Normal | 164,000 ± 95,100 |
| Control: mice infected with *B. suis* 145 | Large | 4,460,000 ± 454,000 |
| Mice vacinaed with 1 ug OPS, infected with *B. suis* 145 | Normal | 908,000 ± 719,000 |
| Mice vaccinated with 100 ug OPS, infected with *B. suis* 145 | Normal | 511,000 ± 246,000 |
| Control: mice infected with *B. melitensis* 16M | Large | 279,000 ± 36,800 |

TABLE 1-continued

Cross-protection study using a previous vaccine formulation

| Group of mice (5 mice/group) | Spleen size | Average number of bacteria (CFU)/spleen |
|---|---|---|
| Mice vaccinated with 1 ug OPS, infected with *B. melitensis* 16M | Normal | 325,000 ± 183,000 |
| Mice vaccinated with 100 ug OPS, infected with *B. melitensis* 16M | Normal | 102,200 ± 18,000 |

By convention, minimal protection is when vaccinates have 10-fold less bacteria in their spleens than unvaccinated controls. The above shows that the former vaccine formulation as disclosed in U.S. Pat. No. 5,951,987 was not protective against *B. melitensis* 16M nor *B. suis* 145. It was also of little effect against *B. abortus* 2308, an unusual strain of *B. abortus* that sometimes changes its antigens to evade the immune system of the mouse (G. G. Schurig, personal communications, 1997). As the previous vaccine, formulated from *B. abortus* 1119-3 (that expresses the "A" OPS) was not protective against *B. melitensis* 16M (that expresses "M" OPS), *B. suis* 145 (that expresses "M" as well as "A" OPS) nor in this case *B. abortus* 2308 (which is variable and sometimes shifts from "A" to "M" OPS), it was apparent that the previous vaccine (as disclosed in U.S. Pat. No. 5,951,987) was limited in its scope of protection. At the time of the previous patent submission, in which the vaccine formulated from *B. abortus* 1119-3 was protective against the species and strains of Brucella tested, this was unobvious. The previous patent and past publication taught away from the new finding that a combination vaccine, one with more than one OPS, was needed for wider protection against Brucella.

As noted in the above table, large doses of *B. abortus* 1119-3 OPS (i.e. 100 ug/mouse) did not offer any advantage for protection and indeed appeared to be counter-protective from *B. abortus* 2308 challenge. The Applicant has observed that low doses are more effective than high doses, one dose is better than three doses, and formulations that enhance antibody production (e.g. OPS on lipopolysaccharide, OPS in liposomes) are counter-productive. Antibody induction is counter-productive because antibody will opsonize, or coat, invading bacteria, these are recognized by white blood cells which ingest the bacterium, and then the parasitic bacterium is inside the host white blood cell, its preferred environment. In contrast, low doses of OPS vaccine appear to stimulate cell-mediated responses (Dr. John Wyckoff, Oklahoma State University, personal communications, 2000).

EXAMPLE 2

Effectiveness of Various Combination Vaccine Candidates on Vaccinated Mice Infected One Day After Vaccination

TABLE 2

Response of vaccinated mice infected one day after vaccination. Median bacterial numbers are shown in brackets. Each group represents five mice. The animals were sacrificed seven days after infection.

| Vaccine given to group | Spleen wt/body wt | Bacterial CFU/spleen |
|---|---|---|
| None, saline control | 0.0211 ± 0.0028 | 2,400,000 ± 250,000 (2,200,000) |
| 1 ug *B. melitensis* OPS | 0.0163 ± 0.0027 | 1,690,000 ± 451,000 (1,860,000) |
| 100 ug *B. melitensis* OPS | 0.0114 ± 0.0007 | 850,000 ± 361,000 (880,000) |
| 0.5 ug *B. melitensis* OPS + 0.5 ug *B. abortus* OPS | 0.0172 ± 0.0012 | 1,820,000 ± 381,000 (2,140,000) |
| 50 ug *B. melitensis* OPS + 50 ug *B. abortus* | 0.0129 ± 0.0015 | 984,000 ± 386,000 (680,000) |
| 0.5 ug *B. melitensis* OPS-protein + 0.5 ug *B. abortus* OPS | 0.0089 ± 0.0003 | 624,000 ± 359,000 (96,000) |
| 50 ug *B. melitensis* OPS-protein + 50 ug *B. abortus* OPS | 0.0183 ± 0.0015 | 1,550,000 ± 351,000 (1,560,000) |

Throughout several years of studying Brucella infections in mice, it was evident that not all infected mice come down with brucellosis. Usually about 5–10% of the mice are infected, as evidenced by Brucella in their spleens, but as the numbers are trivial, they are obviously not developing brucellosis. In the publication by Detilleux et al. (Detilleux, P. G., Deyoe, B. L., and Cheville, N. F. 1990. Penetration and Intracellular Growth of *Brucella abortus* in nonphagocytic cells in vitro. *Infection and Immunity* 58: 2320–2328) it was observed that Brucella takes about 2 hours to infect mammalian cells. The Applicant has also observed over the years that the most virulent forms of Brucella (e.g. *B. melitensis* 16M) shed their OPS, potentially vaccinating the experimental animal before infection. Two questions were asked. Does a combination vaccine protect against more strains and serotypes of Brucella? Does this vaccine work in a very short time frame, such as a day instead of several weeks?

In the above data, initially it appears that none of the vaccine formulations were protective when given a day before infection. That is because a single mouse in a group of 5 that either was not responsive to the vaccine or if the vaccine was not properly administered, will have high bacterial counts that will skew the average. As the data was entered, it was obvious that the one highlighted (0.5 ug *B. melitensis* OPS-protein complex+0.5 ug *B. abortus* OPS)

was actually very protective. In this instance, the median (or the middle number) was more reflective than the average bacterial count. It can also be seen that the vaccine does protect mice against *B. melitensis* 16M infection, even when given as early as a day before infection (and other studies in the Applicant's laboratory at the Defence Research Establishment Suffield (DRES) showed vaccine protection in as little as 1 hour before infection). The potential is that livestock being shipped to an area of high brucellosis prevalence, or a traveller or soldier travelling to a country where Brucella is endemic, can be vaccinated with protection developing as they are en route.

EXAMPLE 3

Effectiveness of Various Combination Vaccine Candidates on Vaccinated Mice Infected Five Weeks After Vaccination

TABLE 3

Response of vaccinated mice infected five weeks after vaccination. Median bacterial numbers are shown in brackets. Each group represents five mice. The animals were sacrificed seven days after infection.

| Vaccine given to group | Spleen wt/body wt | Bacterial CFU/spleen |
|---|---|---|
| None, saline control | 0.0117 ± 0.0015 | 1,120,000 ± 195,000 (1,300,000) |
| 1 ug *B. melitensis* OPS | 0.0066 ± 0.0004 | 48,500 ± 23,000 (44,000) |
| 100 ug *B. melitensis* OPS | 0.0073 ± 0.0002 | 365,000 ± 167,000 (290,000) |
| 0.5 ug *B. melitensis* OPS + 0.5 ug *B. abortus* OPS | 0.0061 ± 0.0004 | 35,800 ± 6,460 (42,000) |
| 50 ug *B. melitensis* OPS + 50 ug *B. abortus* | 0.0065 ± 0.0005 | 162,000 ± 70,000 (150,000) |
| 0.5 ug *B. melitensis* OPS-protein + 0.5 ug *B. abortus* OPS | 0.0059 ± 0.0003 | 67,600 ± 30,200 (92,000) |
| 50 ug *B. melitensis* OPS-protein + 50 ug *B. abortus* OPS | 0.0069 ± 0.0004 | 85,100 ± 26,000 (70,000) |

The results shown in Tables 2 and 3 above, demonstrate that overall, 0.5 ug *B. melitensis* OPS-protein+*B. abortus* OPS was most effective in providing protection against *B. melitensis* 16M infection, either one day or five weeks after vaccination. Higher dose of the same vaccine does not seem to be as effective, probably because it elicit antibodies. Tables 2 and 3 also show that given several weeks, OPS vaccines are effective for protecting mice from *B. melitensis* 16M infections.

EXAMPLE 4

Effectiveness of Different Vaccine Candidates Against Different Species and Strains of Brucella Infections In this case, Balb/c mice were vaccinated by the intraperitoneal route with various vaccine candidates. The mice were challenged (i.p.) four weeks later with different species of Brucella. One week after infection, the mice were sacrificed and assessed for brucellosis. Each group represents the average for five mice, each mouse was given 1 ug of each OPS.

TABLE 4

Effect of various vaccines against different type of *Brucella* infections.

| | Spleen wt/body wt (first line)<br>Bacterial count (CFU) in spleen (second and third line) | | | |
|---|---|---|---|---|
| | *B. melitensis* 16M infection | *B. suis* 145 infection | *B. abortus* 30 infection | *B. abortus* 2308 infection |
| Control - no vaccine | 0.0162 ± 0.0025<br>3,470,000 ± 740,000 | 0.0052 ± 0.0008<br>346,000 ± 74,900 | 0.0080 ± 0.0008<br>970,000 ± 191,000 | 0.0047 ± 0.0004<br>155,000 ± 74,300 |
| *B. abortus* OPS vaccine | 0.0077 ± 0.0012<br>270,000 ± 136,000 | 0.0052 ± 0.0003<br>91,200 ± 20,500 | 0.0077 ± 0.0014<br>391,000 ± 146,000 | 0.0055 ± 0.0010<br>7,740 ± 4,030 |
| *B. suis* OPS vaccine | 0.0055 ± 0.0003<br>6,650 ± 2,310 | 0.0045 ± 0.0003<br>20 ± 11 | 0.0048 ± 0.0005<br>148 ± 91 | 0.0050 ± 0.0005<br>9,920 ± 5,090 |
| *B. melitensis* OPS-protein | 0.0059 ± 0.0006<br>25,900 ± 13,800 | 0.0045 ± 0.0004<br>0 ± 0 | 0.0051 ± 0.0004<br>108 ± 59 | 0,0065 ± 0.0008<br>238,000 ± 77,400 |
| *B. abortus* OPS + *B. melitensis* OPS-protein | 0.0055 ± 0.0004<br>36,900 ± 16,400 | 0.0052 ± 0.0005<br>12 ± 5 | 0.0045 ± 0.0006<br>212 ± 212 | 0.0053 ± 0.0005<br>112,000 ± 63,300 |

TABLE 4-continued

Effect of various vaccines against different type of *Brucella* infections.

| | Spleen wt/body wt (first line) Bacterial count (CFU) in spleen (second and third line) | | | |
|---|---|---|---|---|
| | *B. melitensis* 16M infection | *B. suis* 145 infection | *B. abortus* 30 infection | *B. abortus* 2308 infection |
| *B. abortus* OPS + *B. melitensis* OPS-protein + *B. suis* OPS | 0.0037 ± 0.0002<br>(no water 1 day)<br>44,700 ± 31,400 | 0.0048 ± 0.0004<br>1 ± 1 | 0.0050 ± 0.0003<br>56 ± 51 | 0.0052 ± 0.0004<br>84,900 ± 32,600 |

The above results show that either a combination of OPS and OPS-protein antigens from different Brucellae, or an OPS preparation from a single strain of Brucella, (for example *B. suis* 145) that expresses more than one OPS, were effective in protecting mice from brucellosis. The most remarkable of the vaccine "cocktails" tested is that of *B. suis* 145 OPS. It not only protects against a very wide range of Brucella species, but it also appears to work the best for each. It is believed that this greater OPS vaccine protection is because *B. suis* 145 not only expresses both "A" and "M" (instead of just one) OPS, but that it also expresses one (which Dr. Brad Berger at DRES has isolated) or more additional and previously unknown OPS.

It is also interesting to note that the vaccines work best (i.e. there is a greater contrast between non-vaccinated control mice and vaccinated mice) for the species and strains of Brucellae that are the most virulent (i.e. species or strains of Brucella that cause a large spleen sizes and high bacterial numbers in the spleens of unvaccinated animals). OPS is on the surface of smooth Brucella and it is also shed by the most virulent species and strains of Brucella. It is now believed that the OPS is a virulence factor that reduces the resistance of the host. By vaccinating with OPS and inducing an immunity against this component, it is likely that the host has an immunity both against the Brucella bacterium but also against the OPS that they shed.

EXAMPLE 5

Effectiveness of Different Vaccine Candidates Using Various Administration Routes In this case, mice were vaccinated by different routes and various vaccines candidates were used. The mice were challenged four weeks after vaccination with different species of Brucella and were sacrificed and assessed one week after vaccination. Each group represents the average of 15 mice and each mouse was given 1 ug of OPS.

TABLE 5

Effectiveness of different vaccine candidates using various administration of vaccine routes.

| | Spleen wt/body wt Bacterial count (CFU) in spleen | | | |
|---|---|---|---|---|
| | *B. melitensis* 16M challenge, i.n. | *B. suis* 145 challenge, i.n. | *B. abortus* 30 challenge, i.n. | *B. abortus* 2308 challenge, i.n. |
| Saline control, i.m. | 0.0082 ± 0.0004<br>124,000 ± 34,900 | 0.0117 ± 0.0010<br>448,000 ± 122,000 | 0.0047 ± 0.0001<br>87 ± 24 | 0.0052 ± 0.0001<br>7,040 ± 2,540 |
| *B. suis* OPS, i.n. | 0.0088 ± 0.0004<br>288,000 ± 90,100 | | | |
| *B. suis* OPS, i.m. | 0.0071 ± 0.0004<br>288,000 ± 90,100 | 0.0082 ± 0.0006<br>48,500 ± 14,900 | 0.0045 ± 0.0001<br>65 ± 27 | 0.0048 ± 0.0001<br>954 ± 523 |
| *B. abortus* OPS + *B. melitensis* OPS-protein + *B. suis* OPS, i.m. | 0.0065 ± 0.0002<br>22,000 ± 10,600 | 0.0067 ± 0.0005<br>31,400 ± 11,600 | 0.0045 ± 0.0001<br>20 ± 7 | 0.0050 ± 0.0003<br>125 ± 68 |
| Saline control, s.c. | 0.0074 ± 0.0004<br>62,000 ± 21,900 | 0.01127 ± 0.0010<br>339,000 ± 94,400 | 0.0049 ± 0.0001<br>230 ± 99 | 0.0052 ± 0.0001<br>6,690 ± 2,040 |
| *B. suis* OPS, s.c. | 0.0060 ± 0.0005<br>15,900 ± 12,000 | 0.0072 ± 0.0005<br>29,000 ± 7,680 | 0.0046 ± 0.0002<br>53 ± 19 | 0.0050 ± 0.0001<br>361 ± 179 |
| *B. abortus* OPS + *B. melitensis* OPS-protein + *B. suis* OPS, s.c. | 0.0064 ± 0.0002<br>7,100 ± 1,980 | 0.0070 ± 0.0004<br>25,000 ± 6,000 | 0.0047 ± 0.0001<br>31 ± 20 | 0.0047 ± 0.0001<br>154 ± 65 |

The above shows that either a "cocktail" vaccine, made by adding purified antigens from different bacteria or by adding different antigens prepared from one bacterium, given by different routes can protect mice from a wide range of different Brucella species and strains.

Recently the *B. suis* 145 OPS vaccine (1 ug/mouse) was given to anaesthetized mice (female, balb/c) by the intranasal route and mice were challenged 4 weeks later with *B. suis* 145 also given intra-nasally. Administration by this route did not appear to offer any protection. At the Applicant's research establishment, it has been observed that vaccination against other infectious bacteria by the intranasal route appears to induce antibodies in the respiratory tract (Dr. Bill Kournikakis, unpublished data). The induction of antibodies is counter-productive for vaccine protection against Brucella. Recently it has been found that *B. suis* 145 OPS offers protection in mice from brucellosis when given in doses ranging from 1 ng to 100 ug. It was not protective when doses were less than a nanogram. It is likely that this vaccine can be effective for protecting mice from brucellosis when given intranasally, but that the lower doses, in the nanogram rather than microgram range, must be used to induce a cell-mediated response and to avoid a counter-productive antibody response.

EXAMPLE 6

Passive Immunity

Mice were vaccinated with 1 ug *B. suis* OPS intraperitoneally. An hour later these were sacrificed and their serum collected. Half a ml of serum was given to each naïve mouse about 3 hours later. Recipient mice were challenged with *B. melitensis* 16M an hour after receiving the noted serum. The results are shown in Table 6.

TABLE 6

Passive Immunity

| Group | Mouse | Mouse wt. (g) | Spleen wt (g) | Bacteria in spleen |
|---|---|---|---|---|
| CONTROL - mice received 0.5 ml of serum from unvaccinated mice. Infected 1 hr later, assessed 1 week later | 1 | 23.52 | 0.4034 | 5,370,000 |
| | 2 | 21.28 | 0.4682 | 4,280,000 |
| | 3 | 22.24 | 0.4491 | 2,000,000 |
| | 4 | 20.56 | 0.4027 | 1,860,000 |
| | 5 | 23.36 | 0.4618 | 2,580,000 |
| TEST - mice received 0.5 ml of serum from vaccinated mice. Infected 1 hr later, assessed 1 week later. | 1 | 21.82 | 0.1174 | 620,000* |
| | 2 | 19.52 | 0.4663 | 260,000* |
| | 3 | 24.66 | 0.2162 | 1,000,000 |
| | 4 | 21.64 | 0.6244 | 0 |
| | 5 | 21.52 | 0.6765 | 2,360 |

*colonies were unusually small

The above shows that protection against brucellosis is very rapid (protection occurs within 1 hour of being vaccinated) and that this protection can be transferred by giving immune serum to naive mice to give them protection as well.

EXAMPLE 7

Passive Immunity (Continued)

In a second passive immunity study, mice were vaccinated with 1 ug each with *B. melitensis* 16M OPS-protein given i.p, sacrificed four weeks later, and their blood was fractionated. Naive mice (Table 7), were recipients (the number of mice used was small for this was proof of concept to justify further study). A control mouse was given saline intraperitoneally. For the other groups, these received (from the first set of sacrificed mice) their red blood cells (0.5 ml/mouse), serum (0.5 ml/mouse) or washed white blood cells (in 0.3 ml saline/mouse). Mice given these injections were challenged one day later with $5\times10^4$ bacteria given intra-peritoneally, and were sacrificed and assessed one week later.

TABLE 7

Passive Immunity

| Mice were given: | Mouse | Body wt (g) | Spleen wt. (g) | Bacteria in spleen |
|---|---|---|---|---|
| Saline | 1 | 37.44 | 0.7547 | 5,340,000 |
| Red blood cells | 1 | 37.52 | 0.4737 | 2,980,000 |
| | 2 | 39.18 | 0.8639 | 2,840,000 |
| | 3 | 37.12 | 0.7522 | 2,480,000 |
| White blood cells | 1 | 35.52 | 0.4611 | 740,000 |
| | 2 | 36.86 | 0.3960 | 1,860,000 |
| | 3 | 36.40 | 0.5360 | 1,000,000 |
| Serum | 1 | 39.66 | 0.4098 | 440,000 |
| | 2 | 35.06 | 0.3956 | 2,500,000 |
| | 3 | 37.92 | 0.2497 | 280,000 |

The above shows that in vaccinated mice, the protective factor appears to be made in white blood cells and then released into the serum. This protective factor is produced rapidly (within 1 hour as evidenced by Table 6), continues to be produced for several weeks (as evidenced by the above Table 7) and can be transferred to naive mice to offer them protection from brucellosis as well.

We claim:

1. An immunogenic composition comprising a combination of Brucella "A" outer-polysaccharide and Brucella "M" outer-polysaccharide and Brucella "R" protein antigens, wherein said immunogenic composition is at least free of LPS in an amount obtainable by centrifugation.

2. An immunogenic composition as claimed in claim 1, wherein said Brucla "A" outer-polysaccharide and Brucella "M" outer-polysaccharide are at least 90 percent pure.

3. An immunogenic composition as claimed in claim 1, wherein said Brucella of the Brucella "A" outer-polysaccharide is a Brucella species selected from the group consisting of *B. abortus* biovar 1, *B. abortus* biovar 2, *B. abortus* biovar 3, *B. abortus* biovar 6, *B. melitensis* biovar 2, *B. suis* biovar 1, *B. suis* biovar 2, *B. suis* biovar 3, *B. neotomae* and *B. maris;* said "M" outer-polysaccharide is extracted from Brucella species selected from the group consisting of *B. abortus* biovar 4, *B. abortus* biovar 5, *B. abortus* biovar 9, *B. melitensis* biovar 1, and *B. suis* biovar 5; and said "R" antigens are protein, core polysaccharide and outer-polysaccharide and Brucella of said Brucella "R" antigens is a Brucella species selected from the group consisting of *B. ovis* and *B. canis.*

4. An immunogenic composition as claimed in claim 1, wherein said Brucella of said Brucella "A" outer-polysaccharide and said Brucella of said "M" outer-polyssccharide are independently selected from a Brucella species selected from the group consisting of *B. abortus* biovar 7, *B. melitensis* biovar 3 and *B suis* biovar 4, and said Brucella of the Brucella "R" antigens is a Brucella species selected from the group consisting of *B. ovis* and *B. canis.*

5. An immunogenic composition comprising a combination of Brucella outer-polysacoharides comprising Brucella "A" outer-polysaccharide, Brucella "M" outer-polysaccharide and a Brucella outer-polysaccharide-protein complex, wherein said immunogenic composition is at least free of LPS in an amount obtainable by centrifugation.

6. An immunogenic composition as claimed in claim 5, wherein said outer-polysaccharides are at least 90 percent pure.

7. An immunogenic composition as claimed in claim 5, wherein said Brucella of the Brucella "A" outer-polysaccharlde is a Brucella species selected from the group consisting of *B. abortus* biovar 1, *B. abortus* biovar 2, *B. abortus* biovar 3, *B. abortus* biovar 6, *B. melitensis* biovar 2, *B. suis* biovar 1, *B. suis* biovar 2, *B. suis* biovar 3, *B. neotomae* and *B. maris;* said Brucella of the Brucella "M" outer-polysaccharide is a Brucella species selected from the group consisting of *B. abortus* biovar 4, *B. abortus* biovar 5, *B. abortus* biovar 9, *B. melitensis* biovar 1, and *B suis* biovar 5; and said outer-polysaccharide-protein complex is selected from the group consisting of outer-polysaccharide and Brucella membrane proteins, outer-polysacoharide and Brucella surface proteins, outer-polysaccharide and Brucella surface enzymes and outer-polysaccharide and Brucella cytoplasmic proteins.

8. An immunogenic composition as claimed in claim 5, wherein said Brucella of said Brucella "A" outer-polysaccharide and said Brucella of said "M" outer-polysaccharide are independently selected from a Brucella species selected from the group consisting of *B. abortus* biovar 7, *B. melitensis* biovar 3 and *B. suis* biovar 4, and said outer-polysaccharideprotein complex is selected from the group consisting of outer-polysaccharide and Brucella membrane proteins, outer-polysaccharide and Brucella surface proteins, outer-polysaccharide and Brucella surface enzymes and outer-polysaccharide and Brucella cytoplasmic proteins.

9. An immunogenic composition as claimed in claim 1, wherein each of said outer-polysaccharide is present in an amount equivalent to 1 ng to 100 μg for mice.

10. An immunogenic composition as claimed in claim 9, wherein said outer-polysaccharide is present in an amount equivalent to 1 ug for mice.

11. A prophylactic method of protecting against brucellosis comprising administering to a mammal an immunogenic composition as claimed in claim 1 prior to infection.

12. A method as claimed in claim 11, wherein said immunogenic composition is administered intraperitonally, sub-cutaneously, intra-muscularly, intra-nasally or orally.

13. A prophylactic method of protecting against brucellosis comprising administering to a mammal, serum or white blood cells obtained from mammals administered an immunogenic composition as claimed in claim 1.

* * * * *